(12) United States Patent
Saul

(10) Patent No.: US 8,226,906 B2
(45) Date of Patent: Jul. 24, 2012

(54) SAMPLE COLLECTION DEVICE SUITABLE FOR LOW-VOLUME EXTRACTION

(75) Inventor: David James Saul, Auckland (NZ)

(73) Assignee: Zygem Corporation Limited, Hamilton (NZ)

(*) Notice: Subject to any disclaimer, the term of this patent is extended or adjusted under 35 U.S.C. 154(b) by 196 days.

(21) Appl. No.: 12/554,822

(22) Filed: Sep. 4, 2009

(65) Prior Publication Data
US 2010/0226826 A1  Sep. 9, 2010

Related U.S. Application Data

(60) Provisional application No. 61/095,271, filed on Sep. 8, 2008.

(51) Int. Cl.
| | |
|---|---|
| G01N 21/75 | (2006.01) |
| G01N 31/22 | (2006.01) |
| G01N 33/52 | (2006.01) |
| G01N 1/00 | (2006.01) |
| G01N 1/18 | (2006.01) |
| G01N 1/12 | (2006.01) |
| B04B 1/00 | (2006.01) |
| B01L 3/14 | (2006.01) |

(52) U.S. Cl. ........ 422/406; 422/411; 422/548; 422/549; 436/174; 436/178; 73/864.72

(58) Field of Classification Search .......... 422/405, 422/406, 548, 549; 436/174, 178; 73/864.72
See application file for complete search history.

(56) References Cited

U.S. PATENT DOCUMENTS

| | | | |
|---|---|---|---|
| 4,101,467 A | 7/1978 | Park et al. | |
| 4,639,487 A | 1/1987 | Hazelton et al. | |
| 5,031,635 A | 7/1991 | Koll | |
| 5,084,005 A | 1/1992 | Kachigian | |
| 5,735,808 A * | 4/1998 | Delgado et al. | 604/1 |
| 6,312,395 B1 | 11/2001 | Tripp et al. | |
| 6,388,043 B1 * | 5/2002 | Langer et al. | 528/80 |
| 6,475,165 B1 | 11/2002 | Fournier | |
| 7,309,469 B2 | 12/2007 | Anderson et al. | |
| 2001/0008614 A1 * | 7/2001 | Aronowitz | 422/101 |
| 2003/0049833 A1 | 3/2003 | Chen et al. | |
| 2003/0157728 A1 * | 8/2003 | Uhl et al. | 436/177 |
| 2006/0147249 A1 | 7/2006 | Fuller | |
| 2007/0031914 A1 * | 2/2007 | Zhu et al. | 435/25 |

OTHER PUBLICATIONS

"DNA ID™ System-Small Sample Casework Protocol," *Promega Technical Bulletin* 2006.
*Cleaning Validation in active pharmaceutical ingredient manufacturing plants.* (Sep. 1999)The Active Pharmaceutical Ingredients Committee (APIC).
Montpetit, S.A. et al. (2005). "A Simple Automated Instrument for DNA Extraction in Forensic Casework," *Journal of Forensic Science* 50:1-9.

(Continued)

Primary Examiner — Jill Warden
Assistant Examiner — Charles D Hammond
(74) Attorney, Agent, or Firm — Morrison & Foerster LLP

(57) ABSTRACT

A sample collection device suitable for low-volume extraction includes a substantially tubular collection vessel having a closed end, an open end, and one or more sidewalls defining a vessel chamber having a vessel volume. The device further includes a swab for sample collection. The swab formed with a substantially closed-celled polymer foam head and the swab is configured for insertion into the collection vessel.

18 Claims, 6 Drawing Sheets

OTHER PUBLICATIONS

Figure 1:
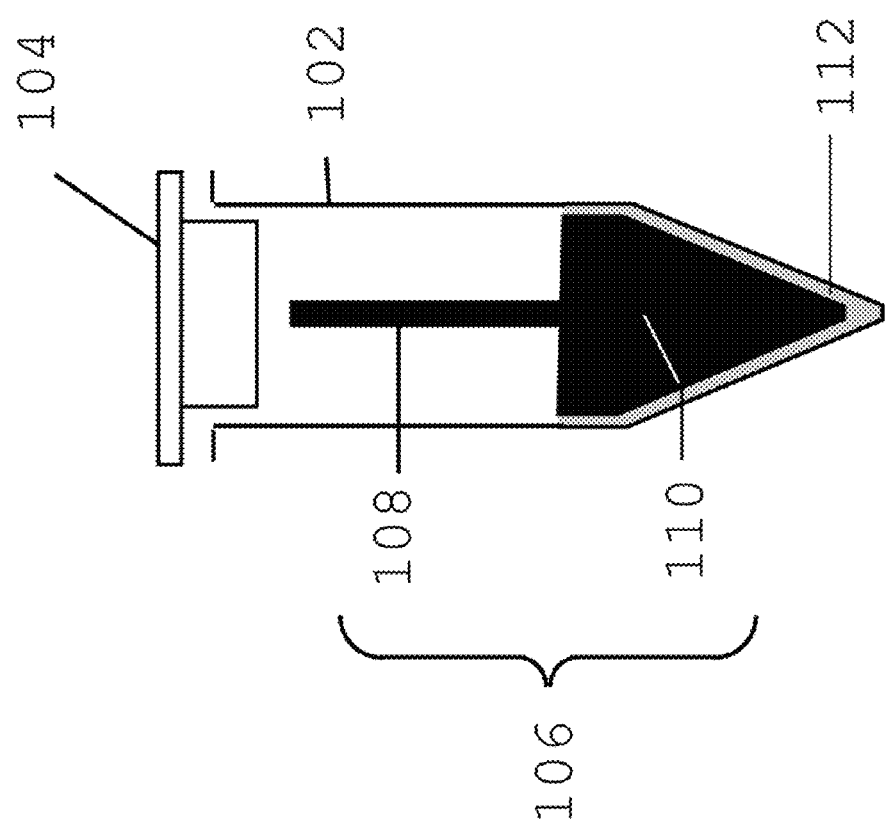
Figure 2:
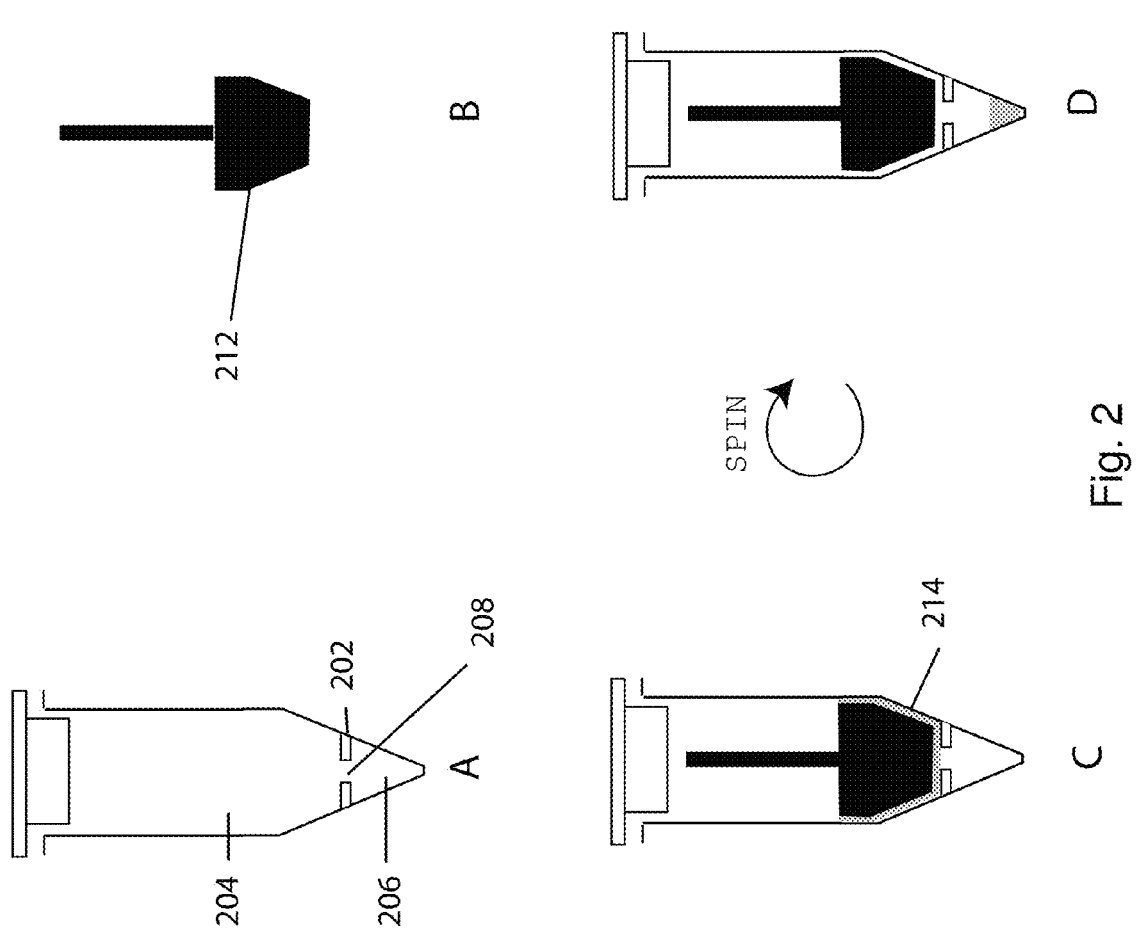

*QIAamp® DNA Mini and Blood Mini Handbook.* Second Edition (Nov. 2007). Quiagen.

Schiffner, L.A. et al. (2005). "Optimization of a simple, automatable extraction method to recover sufficient DNA from low copy number DNA samples for Generation of Short Tandem Repeat Profiles," *Croatian Medical Journal* 46:578-586.

*The Queen versus Sean Hoey.* (Dec. 20, 2007) Neutral Citation No. [2007] NICC 49. Ref WEI7021.

Thompson, R.Q. et al. (1999) "Aqueous recovery from cotton swabs of organic explosives followed by solid phase extraction," *Journal of Forensic Science* 44:795-804.

Van Oorshot, R. et al. (1997). "DNA fingerprints from fingerprints," *Nature* 387:767.

International Search Report and Written Opinion mailed Jan. 26, 2010, for PCT Application No. PCT/NZ09/00188 filed Sep. 7, 2009, 10 pages.

\* cited by examiner

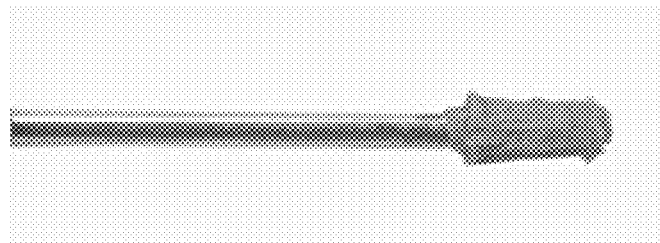
B
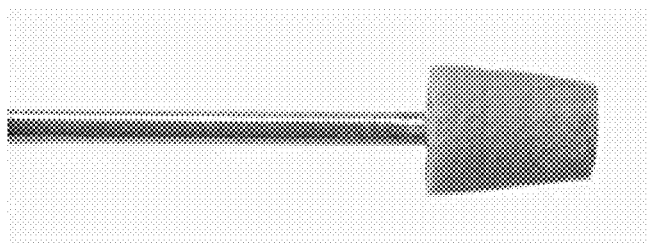
A
Fig. 6

SAMPLE COLLECTION DEVICE SUITABLE FOR LOW-VOLUME EXTRACTION

CROSS REFERENCE TO RELATED APPLICATIONS

This application claims the benefit of U.S. Provisional Application No. 61/095,271, with a filing date of Sep. 8, 2008, which is incorporated herein by reference in its entirety.

BACKGROUND

1. Field

The present application relates generally to sample collection devices, and more specifically, to collection devices suitable for low-volume extraction.

2. Related Art

Frequently, substances must be detected that are present in only trace quantities. This is true for chemical agents, such as explosives and pharmaceuticals, and biological agents, such as microorganisms or trace amounts of nucleic acids. Commonly, these agents are obtained by swabbing a surface and then the swab is used to transfer the material to a vessel containing diagnostic reagents or a solution to extract the agents of interest.

An underlying problem with this strategy is that the swab requires the agent to be removed by using a washing solution and this step dilutes the concentration of the agent making it more difficult to detect. Two strategies are generally used to alleviate this limitation:

1. If the material is solid (for example whole cells), then it is sedimented from the swab eluate by centrifugation and/or filtration prior to extraction. If the agent is soluble, then substances can be added to the washing solution to aid precipitation of the agent thereby making it amenable to concentrating by centrifugation.

2. The sample is extracted in the large volume of solution and then the extractive is concentrated for analysis.

An example where these methods can be used is in the detection of trace (i.e., low copy number (LCN)) nucleic acids in forensic samples.

There are a number of situations where strategy 1 is used. For example, in U.S. Pat. No. 6,475,165 the cells from cervical swabs are washed from the sampling device and sedimented by centrifugation. While this method is acceptable for many samples, there are instances where such a method is unacceptable. For example, if a forensic sample is degraded then it is likely that the cells are not intact and so DNA would be solublized and therefore not sedimented by centrifugation. This can be overcome by washing the collection device in ethanol or isopropanol but such an action results in the nucleic acid being presented to subsequent steps in the presence of alcohols.

The most widely used methods for trace nucleic acid sampling follow strategy 2 and commercial kits are available (DNA IQ™ (Promega, Madison, Wis., USA) and QiaAmp® (Qiagen, Valencia, Calif., USA).

One system takes the extract and then binds the nucleic acids to paramagnetic beads that are concentrated by using a magnet. Although this system is an effective method for concentrating the nucleic acid from the solvent, the procedure has many steps that can only be automated using specialist equipment. More importantly for forensic samples, it requires the tube to be opened several times and so enhances the risk of contamination from extraneous nucleic acid. Ref. 1.

The filtration/column methods use silica or charged resin columns that bind the nucleic acid. These systems also require a number of additional steps for loading, washing and elution of the nucleic acid. For automation, vacuum manifolds are often used and these present a risk of contaminating, extraneous nucleic acid material being drawn through the column. Ref. 2.

DNA extraction using these methods can be automated but in general they require customized robotic systems. For the QiaAmp® system, the Qiagen Corporation provides a robot known as the QIACube®. In the example shown in the paper by Montpetit et al., the Biorobot EZ1 performs bead-based DNA extraction/concentration. Such equipment generally can only be used for the purpose of their design and therefore can, in some cases, represent a significant outlay for a single-use device. Ref. 6.

Other methods include a concentration step using ultrafiltration through a membrane filter, for example Microcon® columns (Millipore, Bedford, Mass., USA). Ref. 3.

Yet other methods concentrate the nucleic acids by the addition of ethanol or isopropanol to precipitate the DNA or RNA. This is then separated by centrifugation.

Yet other methods concentrate the eluate by using n-butanol which in effect draws the water from the extractive.

Neither of the latter two methods can be readily automated and both risk exposing the sample to extraneous contamination.

LCN Forensic DNA Extraction

The use of LCN DNA in forensic analysis is presents several potential difficulties. Because the samples often contain little DNA (just a few genomes in some cases) the environment surrounding the tube, the people handling the samples, and the laboratory equipment are all often better sources of DNA than the sample itself. Therefore all effort must be made to protect the integrity of the sample. For example, Van Oorschot and Jones reported that DNA on laboratory equipment and on a casework samples persisted for long periods of time. Ref. 4.

A notable example of the outcome of forensic samples being compromised is the case of The Queen v. Sean Hoey, in which the defendant had been previously charged with twenty-nine counts of murder in a terrorist attack in a shopping centre in Omagh, Northern Ireland on the 15 Aug. 1988. Ref. 5. The prosecution relied on LCN DNA tests that, on re-examination, were shown to have "very many unsatisfactory matters". These included the likelihood of cross-contamination in the laboratory with other samples and also in the recovery and storage of the items by the Army, Police and Scene of Crime Officers.

The case demonstrated the potential deficiencies in sampling, storage and laboratory handling of LCN samples, which require very exacting standards.

SUMMARY

In one exemplary embodiment, a sample collection device suitable for low-volume extraction includes a substantially tubular collection vessel having a closed end, an open end, and one or more sidewalls defining a vessel chamber having a vessel volume. The device further includes a swab for sample collection; the swab formed using a substantially closed-celled polymer foam and the swab having an uncompressed volume greater than 25% of the vessel volume, preferably approximating the vessel volume. During use of the exemplary sample collection device, the surface of the swab can be extracted in the small volume of solvent held between the swab and the vessel wall.

DESCRIPTION OF DRAWING FIGURES

FIG. 1 depicts a sample collection device suitable for low-volume extraction.

FIGS. 2A-D depict a sample collection device having a filter ring and suitable for low-volume extraction in conjunction with a centrifuge.

Figure 3:
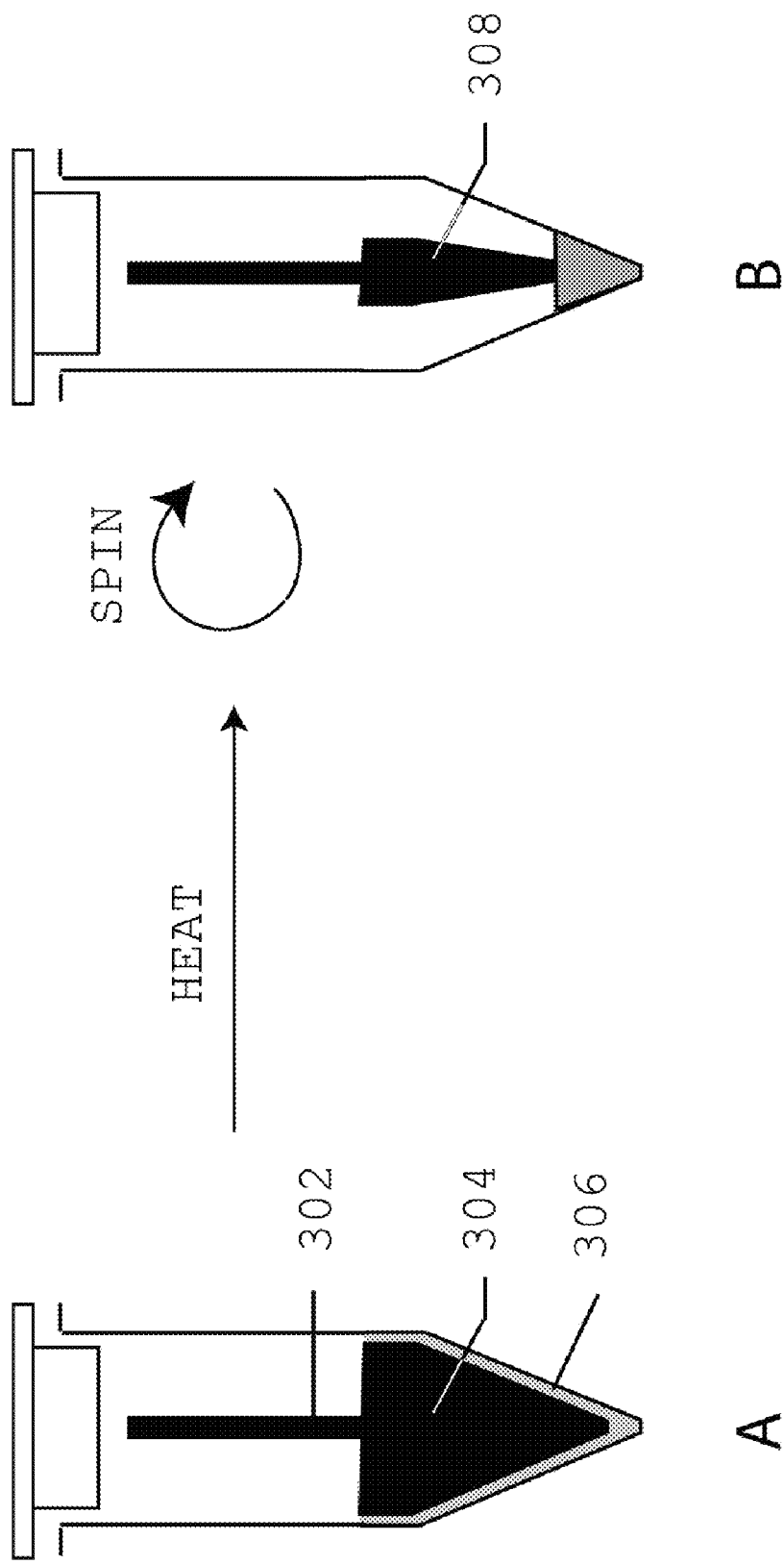

FIGS. 3A and B depict a sample collection device having a swab formed of a heat-shrinkable polymer, prior to heating and centrifugation (3A) and after heating and centrifugation (3B) to extract sample.

Figure 4:
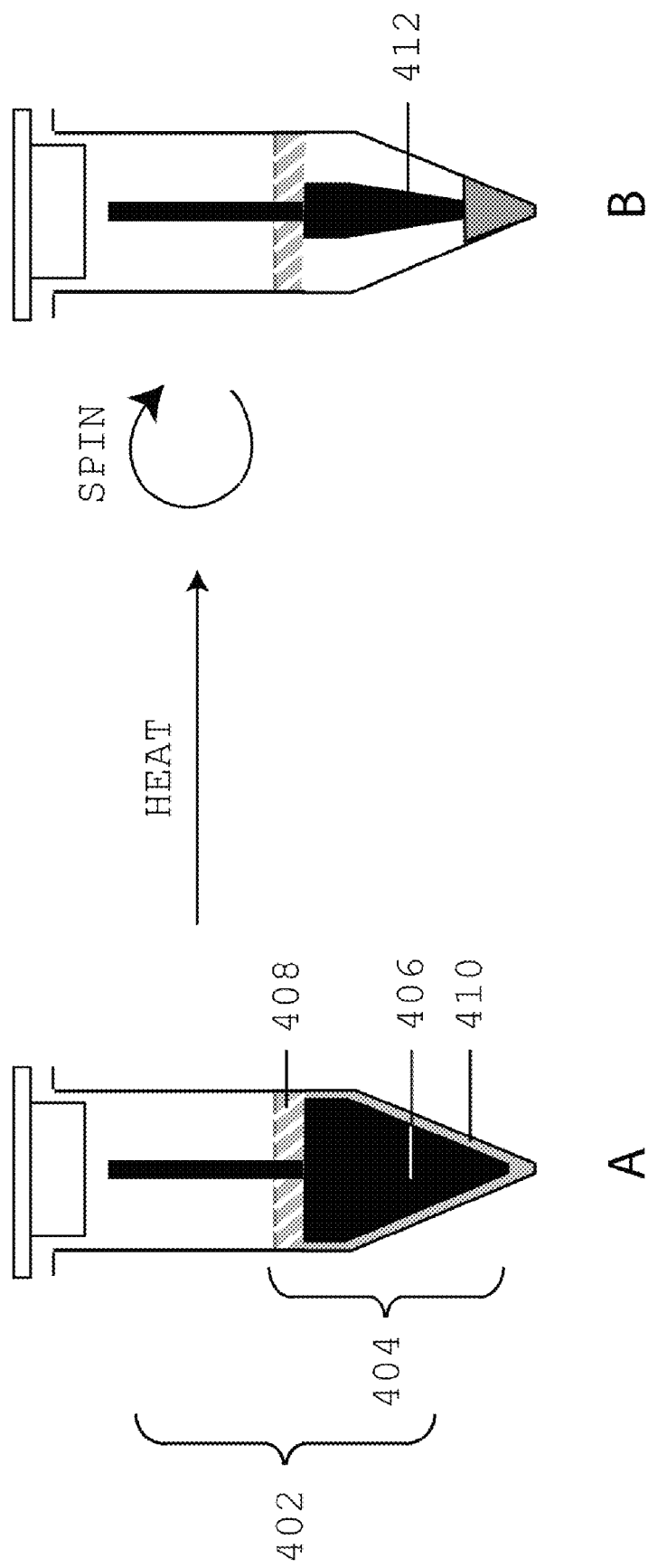

FIGS. 4A and 4B depict a sample collection device having a swab formed of a heat-shrinkable polymer and a non-shrinking seal positioned above the polymer swab prior to heating and centrifugation (4A) and after heating and centrifugation (4B) to extract sample.

Figure 5:
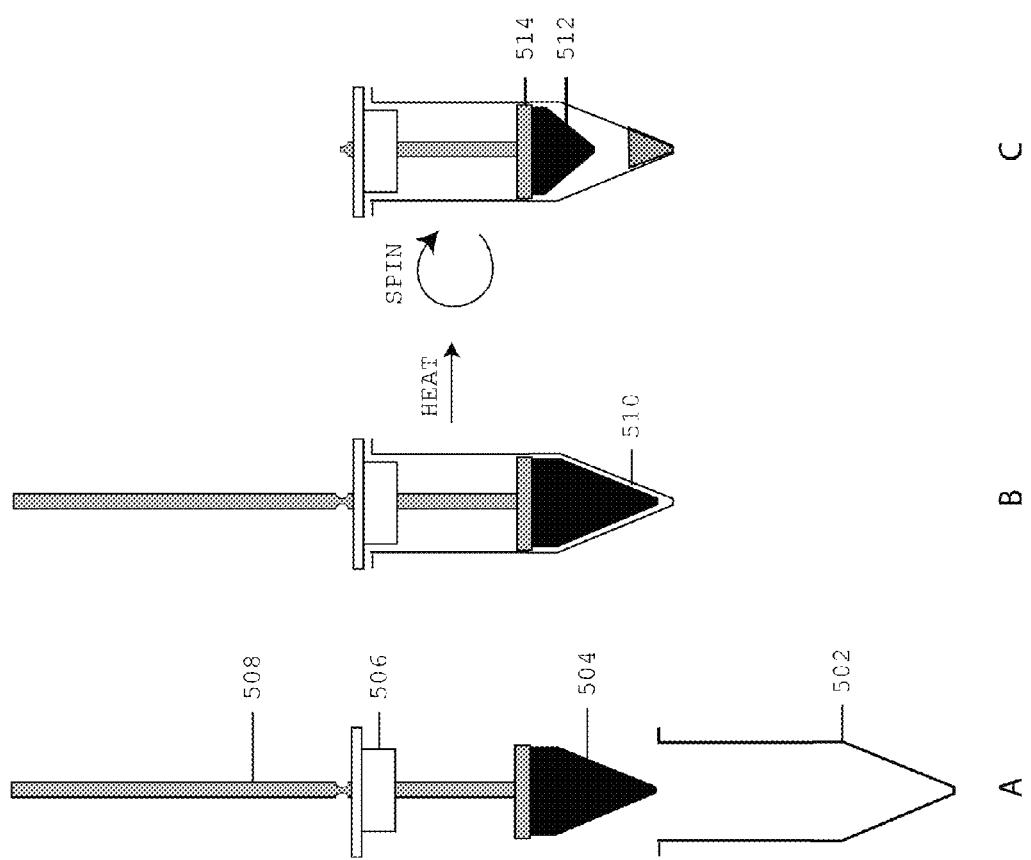

FIGS. 5A-C depict a sample collection device having a integrated lid and collection swab prior to sample collection (5A), after immersion in a sample liquid (5B), and after shrinkage of the foam head of the swab (5C).

FIGS. 6A and 6B depict a heat-shrinkable polyethylene swab, prior to heating (5A) and after heating (5B).

DETAILED DESCRIPTION

The following description sets forth numerous exemplary configurations, parameters, and the like. It should be recognized, however, that such description is not intended as a limitation on the scope of the present invention, but is instead provided as a description of exemplary embodiments.

As described above, it has been observed that sample collection devices may benefit from a capability for low-volume extraction, reduced need for processing, and reduced need for specialized equipment or training. Described herein are sample collection devices having one or more of these beneficial features.

In one embodiment, the sample collection device is suitable for low-volume extraction, which may result in a more concentrated sample. The device includes a collection vessel useful for retaining the sample and for limiting sample contamination. The device further includes a swab for sample collection. The swab is formed using a substantially closed-celled polymer foam, useful for localizing sample material to the external surfaces of the swab and for allowing low-volume extraction. In an embodiment in which the swab is compressible, the swab has an uncompressed volume greater than 25% of the vessel volume. Preferably the swab volume approximates or equals the vessel volume. The sample collection device and methods for its use may be more readily understood in view of the following exemplary devices and methods.

EXAMPLE 1

Sample Collection Device

FIG. 1 depicts a sample collection device 100 formed of a collection vessel 102, a lid 104, and a swab 106. Swab 106 includes an integral handle 108 and a polymer foam head 110. Collection device 100 is depicted after collection of sample, present as liquid layer 112, present on the outer surfaces of polymer foam head 110.

In the present embodiment, collection vessel 102 is a conventional micro-centrifuge tube formed of polypropylene. Lid 104 is connected to vessel 102 via an integral hinge (not shown). Vessel 102 has an internal volume of approximately 2 μL. In some embodiments, the vessel volume is less than 5 μL. In other embodiments, the vessel volume is between 0.5 μL and 5.0 μL. It is understood that the collection vessel may be any convenient collection vessel, preferably impermeable to liquids and gases, once capped. Preferred embodiments include tubular vessels formed of substantially non-reactive materials such as appropriate plastics and glasses. In alternative embodiments, the vessel may present a range of internal volumes, though it is preferable to maintain a volume not substantially greater than the anticipated sample volume (e.g., less than 50 times the intended sample volume). The lid may be integrally formed, as with lid 104, or separately formed. In preferred embodiments, the lid is capable of providing a hermetic seal upon closure, so as to limit loss of sample and contamination.

As depicted in FIG. 1, swab 106 includes a handle 108 embedded in a foam head 110. Preferably, the handle has one or more of the following characteristics: a length short enough to fit inside a closed collection vessel, detachability, or integral formation with the lid. Foam head 110 is formed of a substantially close-celled polyethylene foam, such as a foam described in U.S. Pat. No. 4,101,467. In alternative embodiments, the foam is an olyethylene, polystyrene, polyvinyl chloride, polypropylene, polyurethane, latex, silicone, fluropolymer, ethylene vinyl acetate, or latex foam. Composite foams formed of one or more polymers may also be used.

Preferably, open cells form less than 10%, or less than 5%, of the cells in the foam. Preferably, the material of the foam head exhibits low water absorption capacity due to the low percentage of open cells. In the context of this disclosure, water absorption capacity is defined as grams of water absorbed per gram of the foam, when a cube of the foam, having a volume of 1 $cm^3$, is immersed in distilled water for 24 hours at 23° C. A preferred material for the foam head has a water absorption capacity of less than 2 grams water/gram foam, 1.5 grams water/gram foam, 1 grams water/gram foam, or 0.5 grams water/gram foam. Density of the foam head material is preferably less than 2.0 grams/$cm^3$, 1.5 grams/$cm^3$, 1.0 grams/$cm^3$, or 0.5 grams/$cm^3$.

As depicted, foam head 110 has a geometry substantially similar to the base of vessel 102. In the embodiment of FIG. 1, foam head 110 has an uncompressed volume approximately equal to or slightly less than the volume presented by the corresponding base portion of vessel 102. Accordingly, foam head 110 is depicted in an uncompressed state that allows for a close fit. Preferably, foam head is sized so as to have an uncompressed volume that is equal to or less than the internal volume of the portion of the collection vessel occupied by foam. Accordingly, it is preferable that foam head can be inserted into the collection vessel without significant compression. Preferably, foam head is 100%, 95%, 90%, 85%, 80%, 75%, 70%, 65%, 60%, 55%, 50%, or less than 50% of the internal volume of the collection vessel in the portion of the collection vessel occupied by foam head. The "portion of the collection vessel occupied by the foam head" is understood to be the volume of the collection vessel that is defined by the length of foam head and the walls of the vessel. By way of example, a cylindrical collection vessel having a length of 5 centimeters on the axis running from base to opening for use with a foam head having a length of 3 centimeters, which rests in the cylinder at a position between centimeters 2-4 of the collection vessel when inserted, would have a "portion of the collection vessel occupied by the foam head" equal to the volume of the collection vessel between centimeters 2-4. Accordingly, it is understood that a foam head occupying less than 100% of the portion of the collection vessel occupied by foam head has a diameter less than the diameter of the collection vessel for at least portion of the length of the foam head. In an alternative embodiment, foam head has a diameter slightly larger than that of the collection vessel for at least a portion of the length of the foam head; accordingly, foam head is slightly compressed when inserted in the collection vessel.

Foam head 110 presents surfaces suitable for collection of samples. In a preferred embodiment, at least the surfaces of the foam head are hydrophobic. Generally, the polymer of the foam is hydrophobic, and the property is maintained by avoiding treatments such as application of a hydrophilic solvent or agent.

In an alternative embodiment, the sample collection device is provided with a pre-filled volume of extraction fluid or other reagent, such as an amplification reagent or a profiling/detection reagent. Inclusion of one or more reagents allows for reduced sample handling and risk of contamination.

Sample collection device 100 possesses the following characteristics and features:

A swab that fits snugly into a tube and is compatible with the requirements for processing of the sample.
  Allows minimal extraction volume by forcing the extraction solution to cover a large surface area.
Low absorbency based on use of a substantially closed-cell foam.
  Allows minimal extraction volume.
Hydrophobic surfaces.
  Reduced surface wetting and reduced loss of liquid when the swab is removed;
  Good for collecting hydrophobic samples (for example, cells in the skin oils from fingerprints).

FIGS. 2A-D depict a sample collection device 200. It is understood that device 200 may include one or more of the variations described with reference to device 100. Device 200 is substantially similar to device 100 of FIG. 1, with the following notable differences. Device 200 includes a ring 202 integral to collection vessel 102. Ring 202 divides collection vessel 102 into a first volume 204 and second volume 206. Ring 202 presents an opening 208 such that volumes 204 and 206 are in liquid communication. In an alternative embodiment, the sample collection device includes an alternative separator structure such as a perforated membrane or a filter, which separates the internal volume of the collection vessel into volumes that are in liquid communication.

A swab 212 is depicted in FIG. 2B. Swab 212 may be formed substantially as described for swab 106. Notably, swab 212 presents a geometry designed to accommodate first volume 204, as shown in FIG. 2C, which depicts sample collection device 200 after collection of a liquid sample 214. Liquid sample 214 may be drained away from swab 212 and collected at the bottom of second volume 206 through centrifugation or other suitable technique, as depicted in FIG. 2D.

EXAMPLE 2

Sample Collection Device with Heat Shrinkable Swab

FIGS. 3A and 3B depict a sample collection device 300 having a heat-shrinkable swab 302. It is understood that device 300 may include one or more of the variations described with reference to devices 100 and 200. Generally, device 300 is substantially similar to device 100 of FIG. 1, with the following notable differences. Swab 302 includes a foam head 304 formed of a heat-shrinkable polymer foam. Preferably, the foam exhibits noticeable shrinking at temperatures below 150° C., 125° C., 110° C., or 100° C. A foam capable of shrinking at low temperatures is preferred so as to minimize heat degradation of the sample. Suitable polymers include expanded, cross-linked foams such as those described in U.S. Pat. No. 4,639,487. When cross-linking is used, the heat-shrinkable foam is generally expanded at high temperatures and then rapidly cooled to "fix" the foam in an expanded state. Subsequent heating at an appropriate temperature allows the cross-linkages of the foam to "relax" back to their lower volume state, resulting in shrinking of the foam. While heat-shrinkable polyethylene foams are preferred, it is understood that any conventional heat-shrinkable foam polymer may be used. FIGS. 5A and 5B are actual photographs of a heat shrinkable polyethylene foam swab before (FIG. 5A) and after (FIG. 5B) heat shrinking at 99° C. for 5 minutes. Preferably, the heat shrinkable foam has a pre-heating to post-heating volume ratio of less than 1.5:1, 2:1, 3:1, 4:1, or 5:1. Alternatively, the heat shrink capability of the foam may be assessed under fixed conditions. A preferred heat shrinkable foam has a pre-heating to post-heating volume ratio, when heated at 99° C. for 5 minutes, of less than 1.5:1, 2:1, 3:1, 4:1, or 5:1.

FIG. 3A depicts device 300 after collection of a liquid sample 306. After heating and centrifugation, foam head 304 has shrunken in volume to form shrunken foam head 308, as seen in FIG. 3B. Liquid sample 306 as collected at the bottom of vessel 102, in the void space created by the shrinking of foam head 304. Accordingly, device 300 allows for low-volume sample extraction with minimized sample handling and risk of contamination.

FIGS. 4A and 4B depict a sample collection device 400 having a heat-shrinkable swab 402 including a composite foam head 404. It is understood that device 400 may include one or more of the variations described with reference to devices 100, 200, and 300. Foam head 404 includes heat-shrinkable lower foam 406 and non-heat-shrinkable upper foam 408.

FIG. 4A depicts device 400 after collection of a liquid sample 410. After heating and centrifugation, lower foam 406 has shrunken in volume to form shrunken lower foam head 412, as seen in FIG. 4B. Liquid sample 410 as collected at the bottom of vessel 102, in the void space created by the shrinking of lower foam 406. In comparison, upper foam 408 has not exhibited substantial shrinkage and maintains a close fit with the sidewalls of collection device 102. Thus, upper foam 408 reduces potential evaporation and loss of solvent into an upper air space 414 of the collection vessel. Accordingly, device 400 allows for low-volume sample extraction with minimized sample handling, risk of contamination, and evaporative loss of sample.

A further enhancement includes the addition of a non-shrinking seal above the swab (FIG. 3B). This enhancement would reduce evaporation into the upper air space during heating.

EXAMPLE 3

Sample Collection Device with Integrated Lid and Swab

FIGS. 5A and 5B depict a sample collection device 500 having a separate tube 502, a heat-shrinkable composite foam head 504 and integrated lid 506 and a detachable handle 508. It is understood that device 500 may include one or more of the variations described with reference to devices 100, 200, 300 and 400.

FIG. 5B depicts device 500 after the swab has been immersed in a liquid 510. The dimensions of the foam head conform closely to the internal dimensions of the tube 502 thereby reducing the volume of liquid required to completely cover the swab. The circular flange 514, which can be an integral part of the handle, can be made with dimensions and materials that act as a vapor seal to reduce evaporation on heating in a manner similar to the upper foam layer 408 in example 400.

FIG. 5C depicts the conformation of the swab head after heating the sample to promote shrinkage 512. On heating the foam head shrinks creating a void space for the liquid to collect after centrifugation. By being attached to the tube lid 506, the shrunken swab head is held clear of the liquid thereby preventing capillary and surface wetting of the swab after centrifugation and in so doing improves the recovery of the extractive.

EXAMPLE 4

EA1 Proteinase Extraction of DNA

The device of FIGS. 1-5 may be used for the collection and processing of trace samples whether they are forensic samples or other trace samples from which nucleic acids are to be extracted. In these cases, the tube to be used would be a thermal cycler compatible tube (e.g., a PCR tube). In one preferred embodiment, the DNA extraction method employs EA1 proteinase-based system. Because the EA1-based system allows extracts to be used directly in downstream PCR-based applications, the device would enable samples to be obtained in the field using the sample collection devices of FIGS. 1-5. After in-field sample collection, the device is sealed. DNA may then be extracted using a minimal extraction volume.

EXAMPLE 5

Potential Use in Drug Manufacture

The manufacture of pharmaceutical products requires that each batch is not contaminated by a previous manufacturing run or by the cleaning process. Ref. 7. Most commonly, swabs are used for sampling and the collected material is washed from the swab for analysis for example using chromatography (HPLC) or gas chromatography or an evaluation of total organic carbon is now frequently used because of its sensitivity. A swab must present a minimal background and a high recovery. Typically, a 60% recovery rates is considered acceptable but higher recoveries are more desirable. By reducing the volume of the extraction, using a collection swab that closely fits to the tube and in addition using a material that is non-absorbent, wets poorly, or shrinks and so releases the solvent, yields and concentrations are maximized.

EXAMPLE 6

Potential Use in Detection of Trace Explosives

The collection devices described herein may also be used in the detection of traces of explosives either on the devices themselves or after an explosion has occurred. Ref. 8. Again, it is advantageous to collect any residue on a surface that can be extracted in a minimal volume.

REFERENCES

1. DNA IQ™ System-Small Sample Casework Protocol. Promega Technical Bulletin 2006.
2. QIAamp® DNA Mini and Blood Mini Handbook. Second Edition 2007.
3. Schiffner L A, Bajda E J, Prinz M, seestyen J, Shaler R, Caragine, T A. (2005) Optimization of a simple, automatable extraction method to recover sufficient DNA from low copy number DNA samples for Generation of Short Tandem Repeat Profiles. Croat Med. J. 46:578-586.
4. van Oorshot R A H and Jones M K. 1997 DNA fingerprints from fingerprints Nature 387:767.
5. The Queen versus Sean Hoey Dec. 20, 2007 Neutral Citation No. [2007] NICC 49. Ref WEI7021.
6. Montpetit S A, Fitch I T, O'Donnel PT (2005) A Simple Automated Instrument for DNA Extraction in Forensic Casework. J Forensic Sci 50:1-9.
7. Cleaning Validation in active pharmaceutical ingredient manufacturing plants. The Active Pharmaceutical Ingredients Committee (APIC).
8. Thompson, R. Q.; Fetterolf, D. D.; Miller, M. L.; Mothershead, R. F. (1999) Aqueous recovery from cotton swabs of organic explosives followed by solid phase extraction, J. Forensic Sci. 44: 795-804.

I claim:

1. A sample collection device suitable for low-volume extraction, the device comprising:
   a) a collection vessel having a closed end, an open end, and one or more sidewalls defining a vessel chamber having a vessel volume;
   b) a swab for sample collection, the swab comprising a substantially closed-cell polymer foam head, wherein the substantially closed-cell polymer foam head is a heat-shrinkable polymer foam head having a pre-heating to post-heating volume ratio of less than 1.5:1;
   wherein the swab is configured for insertion into the vessel volume.

2. The device of claim 1, wherein the substantially closed-cell polymer foam head comprises polyehylene.

3. The device of claim 1, wherein the substantially closed-cell polymer foam head is an expanded, cross-linked foam.

4. The device of claim 1, further comprising a non-heat shrinkable seal positioned between the open end and the swab, the seal configured to reduce evaporation of a liquid sample during heating.

5. The device of claim 1, wherein the swab comprises one or more outer surfaces that are hydrophobic.

6. The device of claim 1, wherein the substantially closed-cell polymer foam head has a water absorption capacity of less than 0.5 grams of water per gram of foam.

7. The device of claim 1, wherein at least 90% of the swab, by weight, is comprised of the substantially closed-cell polymer foam head.

8. The device of claim 1, wherein less than 10% of the cells of the substantially closed-cell polymer foam head are open cells.

9. The device of claim 1, wherein the substantially closed-cell polymer foam head has a density of 0.5 to 2.0 grams per $cm^3$.

10. The device of claim 1, wherein the vessel volume is less than 5 μL.

11. The device of claim 1 further comprising a separator structure, wherein the vessel chamber is divided into a first volume and a second volume by the separator and wherein the first volume and second volume are in liquid communication.

12. The device of claim 11, wherein the separator is selected from the group consisting of a perforated membrane, a filter, and a ring structure extending from the one or more sidewalls into the vessel chamber.

13. The device of claim 11, wherein the second chamber has a volume that is less than ⅓ of a volume of the first volume.

14. The device of claim 11, wherein the swab resides in the first volume and is prevented from substantially extending into the second volume by the separator.

15. The device of claim 1, further comprising a lid configured to fit the open end of the collection vessel, wherein the swab is integrated into the lid.

16. The device of claim 1, wherein the polymer foam head is uncompressed when inserted into the collection vessel.

17. The device of claim 1, wherein the polymer foam head has a volume less than the volume that is defined by the length of the foam head and the wall of the vessel.

18. The device of claim 17, wherein the volume of the polymer foam head is less than 90% of the volume of the portion of the collection vessel occupied by the foam head.

* * * * *